United States Patent [19]

Robbins

[11] Patent Number: 4,633,971

[45] Date of Patent: Jan. 6, 1987

[54] STETHOSCOPE WITH HIGH FREQUENCY FILTER

[75] Inventor: David L. Robbins, Roseville, Minn.

[73] Assignee: Minnesota Mining and Manufacturing Company, St. Paul, Minn.

[21] Appl. No.: 796,016

[22] Filed: Nov. 6, 1985

[51] Int. Cl.[4] .............................................. A61B 7/02
[52] U.S. Cl. ..................................... 181/131; 181/135
[58] Field of Search ........................ 181/131, 135, 137

[56] References Cited

U.S. PATENT DOCUMENTS

| 2,389,868 | 11/1945 | Olson | 181/131 |
| 3,169,600 | 2/1965 | Thomas | 181/135 |
| 4,270,627 | 6/1981 | Hill | 181/131 |

FOREIGN PATENT DOCUMENTS 951247  7/1974  Canada .................................. 181/20

OTHER PUBLICATIONS

"Report 1192", by Don D. Davis, Jr., George M. Stokes, Dewey Moore, & George L. Stevens, Jr.
"Elements of Acoustics", by J. Blitz, 1964.

*Primary Examiner*—Benjamin R. Fuller
*Attorney, Agent, or Firm*—Donald M. Sell; James A. Smith; David W. Anderson

[57] ABSTRACT

A low-pass filter is incorporated into the binaural tube of a stethoscope to selectively attenuate high frequency noise. The filter includes a small diameter inertance tube communicating with a large volume compliance chamber and is preferably located as far as possible from the chestpiece of the stethoscope to filter noise not only transmitted from the chestpiece, but also transmitted directly to the binaural tube.

10 Claims, 3 Drawing Figures

STETHOSCOPE WITH HIGH FREQUENCY FILTER

BACKGROUND OF THE INVENTION

1. Field of the Invention

The present invention relates to stethoscopes, and particularly those which filter a portion of the sound spectrum transmitted to the user.

2. Description of the Prior Art

In its most basic form, a stethoscope provides for a column of air extending from a body wall of a person to the ears of a user to transmit acoustical energy or sound. It is sometimes desirable to have a stethoscope which is capable of transmitting selected portions of the full range of sound passing through the stethoscope, such as a high frequency portion or a low frequency portion of the sound resulting from the movement of the body wall. A stethoscope which transmits selected portions of the full range of sound may better enable the user to detect various sounds in one frequency range by attenuating sounds of other frequency ranges that may mask the very sounds the user is trying to detect.

One such selective frequency stethoscope is disclosed in Canadian Pat. No. 951,247 wherein the user may rotate a portion of the stethoscope chestpiece to selectively transmit the full frequency range of sound generated or low or high frequency portions thereof. The drawback of the disclosed stethoscope is that the filtering apparatus is located in the chestpiece and is, therefore, distantly removed from the ear pieces of the user. Thus, environmental noise transmitted to the tubing of the stethoscope connecting the chestpiece and the ear pieces does not pass through the filter and is not removed or attenuated.

SUMMARY OF THE INVENTION

The present invention is particularly useful to field medical personnel attempting to discriminate the Korotkoff sounds, which are associated with blood pressure measurement, from high frequency noise both generated by the patient and the environment.

This high frequency noise is attenuated by a low-pass filter which includes an inertance defined by a tube having an outer diameter substantially equal to the inner diameter of the binaural tubing of a stethoscope and a compliance defined by a volume chamber into which the inertance tube opens. The volume chamber has a volume substantially greater than that of the inertance.

The low-pass filter is effective to remove or attenuate high frequency noise transmitted by the chestpiece along with the Korotkoff sounds. In order to also attenuate high frequency noise which is transmitted to the stethoscope tubing at a point other than the chestpiece, the low-pass filter just described is located along the binaural tubing of the stethoscope closely adjacent the ear pieces and removed from the chestpiece.

The inertance of the low-pass filter is preferably a cylindrical tube having an internal diameter of approximately 1.4 mm and a length of approximately 12.7 mm, dimensions which yield a volume of approximately 19.5 mm$^3$. The compliance preferably has a volume of approximately 11,250 mm$^3$, with a length-to-diameter ratio of 2:1 or less. The shape of the compliance is also preferably a cylindrical tube, with the above requirements yielding a diameter of approximately 19.3 mm and a length of approximately 38.6 mm.

The low-pass filter also includes an exit tube communicating with the compliance and substantially coaxial with the inertance tube. The preferred shape of the low-pass filter is thus a large cylindrical tube with two smaller coaxial tubes extending from either end. This shape allows the filter to be inserted in existing stethoscopes by simply cutting the binaural tube and inserting the inertance tube into one cut end and the exit tube into the remaining cut end.

BRIEF DESCRIPTION OF THE DRAWING

The present invention will be more thoroughly described with reference to the accompanying drawings, wherein like numbers refer to like parts in the several views, and wherein.

DESCRIPTION OF THE PREFERRED EMBODIMENTS

Figure 1:
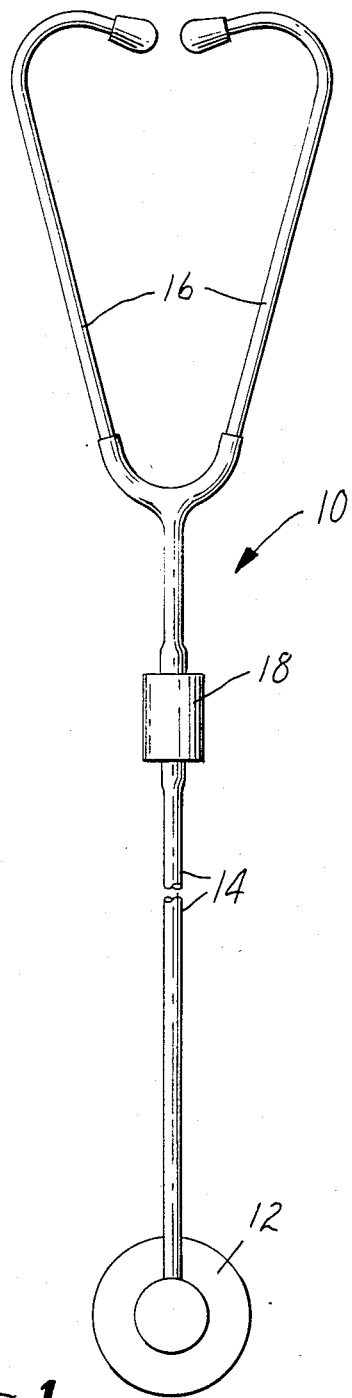
FIG. 1 is a plan view of a typical stethoscope with a low-pass filter of the present invention connected thereto.

The present invention is additions and modifications to a standard stethoscope, generally indicated as 10 in FIG. 1. This standard stethoscope 10 includes a chestpiece 12 for contact with a body cavity of a patient, a bifurcated binaural tube 14 and two ear pieces 16 which together define a headset for connection to the ears of the user.

The chestpiece 12 is conventionally manufactured of metal and includes a diaphragm-covered sound chamber (not shown). The only exception to the conventional nature of the chestpiece 12 is that the diaphragm may be unusually flexible, to emphasize sounds of low frequency. The binaural tube 14 is a hollow, flexible tube preferably manufactured of a rubber or polymeric material. The ear pieces 16 are hollow metal tubes which are inserted into the binaural tube 14.

In operation, the chestpiece 12 is placed over a body cavity of a patient and sound from that body cavity is transmitted from the sound chamber of the chestpiece 12 and along the air column within the binaural tube 14 and the ear pieces 16 to the ears of the user.

The standard stethoscope 10, just described, is useful for transmitting sounds of all frequencies from the body cavity of the patient to the user. No sounds of a particular frequency are attenuated to emphasize sounds at different frequencies. As such, the stethoscope 10 is useful for general diagnosis and a wide range of general medical functions.

It has recently been discovered, however, that there are situations where it would be advantageous to emphasize sounds in a particular frequency over sounds having frequencies outside that band. Emergency medical personnel, such as ambulance attendants, frequently must use a stethoscope in noisy environments. Furthermore, these personnel usually only utilize a stethoscope to perform blood pressure measurements on route to a hospital. Blood pressure measurements are typically made by occluding the brachial artery with a pressure cuff and listening for sounds generated by turbulence in the brachial artery as the pressure in the cuff is slowly released. These particular sounds are named the Korotkoff sounds and have nearly all their acoustical energy in the 50 to 125 Hz band. The present invention emphasizes these Korotkoff sounds by incorporating a low-pass filter 18 within the binaural tube 14 of the stethoscope 10. The low-pass filter 18 operates to selectively attenuate frequencies above 125 Hz and thus emphasizes the Korotkoff sounds generated during blood pressure measurement.

Figure 2:
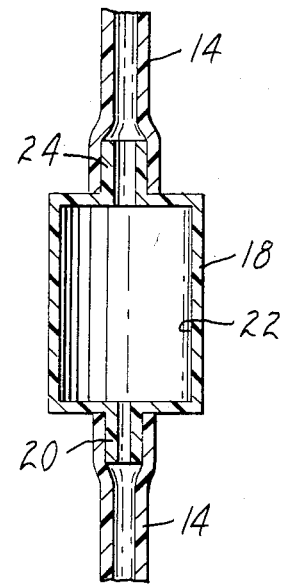
FIG. 2 is a diametral cross-sectional view of the low-pass filter and portions of the stethoscope.

As best seen in FIG. 2, the low-pass filter 18 includes an inertance tube 20, a compliance chamber 22 and an exit tube 24. The inertance tube 20 and the compliance chamber 22 are sized and configured so that their interaction causes a very rapid roll-off or attenuation of sound frequencies above approximately 125 Hz.

An inertance represents the tendency of a mechanical element to resist a change in the volume velocity of a vibrating medium within the element. For a cylindrical configuration, the inertance is proportional to the mass of the medium within the element, and inversely proportional to the square of the cross-sectional area of the element. Thus, for a cylindrical tube, the inertance will increase as the length of the tube increases and the inertance will increase as the cross-sectional area of the tube decreases.

A compliance represents the tendency of a mechanical element to resist a change in the pressure of a vibrating medium within the element. For a cylindrical element this compliance is directly proportional to the volume of the mechanical element and thus increases as its volume increases. Further definition and a more complete description of the relationship between inertance and compliance may be obtained from *Elements of Acoustics,* by J. Blitz, published in 1964 by Butterworth, Inc., Washington, D.C. For purposes of the present invention, however, it is sufficient to understand that sound of a particular frequency may be attenuated by attention to the relationship between the inertance and the compliance and also generally by increasing the value of the inertance and increasing the value of the compliance.

While either an inertance or a compliance alone could be effective to achieve the desired attenuation, practical limits exist as to large increases in the values of the inertance and compliance. If the inertance of the inertance tube 20 is increased, the volume of sound transmitted is proportionately decreased. Thus a very large inertance would decrease the volume of sound transmitted by the low-pass filter 18 to a point where the sound is inaudible. A large increase in the value of the compliance would require a large compliance chamber 22 which would rapidly become unwieldy. However, by combining the two acoustical elements, an inertance and a compliance, the desired attenuation can be achieved in a stethoscope which remains commercially suitable.

With respect to the inertance tube 20 illustrated in FIG. 2, preferred dimensions have been determined to be an inner diameter of approximately 1.4 mm and a length of approximately 12.7 mm. Practical limits on the internal diameter of the inertance tube 20 are approximately 0.5 mm minimum and 2.0 mm maximum. Below the minimum value the inertance of the tube 20 becomes so great that the volume of sound transmitted is reduced to practical inaudibility. Above the maximum internal diameter of the tube 20, the inertance is reduced to such an extent that the inertance tube 20 has no effect on the sound transmitted. The preferred internal dimensions of the compliance chamber 22 are a diameter of approximately 19.3 mm and a length of approximately 38.6 mm which yield a volume of about 11,250 mm$^3$ and a length-to-diameter ratio of 2:1. Ideally, the length-to-diameter ratio of the compliance chamber 22 should be no higher than this 2:1 ratio. A compliance chamber 22 which is exceptionally long and narrow ceases to operate as a single acoustical unit because of localized high and low pressure areas along the length of the compliance chamber 22.

In addition to the important acoustical dimensions described above, the low-pass filter 18 must have an outer diameter of the inertance tube 20 and the exit tube 24 which allows these tubes 20 and 24 to be easily inserted in and yet frictionally retained by the binaural tube 14. The filter 18 may be constructed of any suitable material, such as metal or plastic, with the only limitation being that the filter 18 must have sufficient rigidity to restrict sympathetic vibration in response to sound waves passing therethrough.

Figure 3:
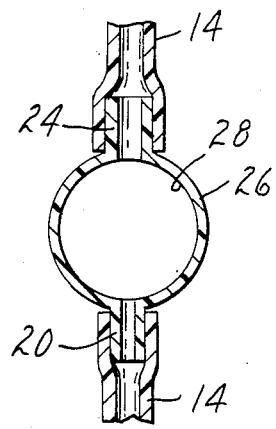
FIG. 3 is a diametral cross-sectional view of a second embodiment of a low-pass filter according to the present invention and portions of the stethoscope.

FIG. 3 illustrates an alternate embodiment of a low-pass filter 26 which has a spherical compliance chamber 28 rather than the cylindrical compliance chamber 22 of the embodiment shown in FIG. 2. The spherical shape of the compliance chamber 28 is acoustically preferred over that of the cylindrical shape of FIG. 2 because the length to diameter ratio is 1:1 and thus well below the desired maximum ratio of 2:1. However, the spherical compliance chamber 28 is difficult to manufacture and so, as a practical matter, cannot be utilized. FIG. 3 does indicate, however, that many different shapes of the compliance chamber 22 may be utilized effectively, and even advantageously.

The low-pass filter 18 of the present invention may be incorporated into existing stethoscopes simply by cutting the binaural tube 14 and forcing the ends of the cut tube 14 over the inertance tube 20 and the exit tube 24. The low-pass filter 18 must be oriented with the inertance tube 20 directed toward the chestpiece 12. An important aspect of the present invention is that the filter 18 may be located anywhere along the binaural tube 14 and thus may be located very near the ear pieces 16 and distantly removed from the chestpiece 12. The advantage of this arrangement is that not only sound coming from the chestpiece 12 is filtered. environmental noise which is transmitted directly through and into the length of the binaural tube 14 also must pass through the low-pass filter 18 and thus is effectively eliminated. This feature is particularly significant to ambulance attendants which may have to use the stethoscope 10 under noisy environmental conditions.

Thus there has been described a low-pass stethoscope filter 18 which may be easily added to existing stethoscopes, which is easy to manufacture and which is effective to filter extraneous noise transmitted not only to the chestpiece 12 of the stethoscope but also to its binaural tube 14.

Although the present invention has been described with respect to only a limited number of embodiments, it is understood that many modifications will be apparent to those skilled in the art. All such modifications falling within the spirt and scope of the appended claims are intended to be included in the invention.

I claim:

1. A low-pass filter for use in the binaural tubing of a stethoscope to attenuate high frequency noise and prevent the transmission of such noise to the user, comprising:

an inertance defined by a tube having an outer diameter sized to frictionally engage the inner diameter of said binaural tubing and an inner diameter substantially less than the inner diameter of said binaural tubing; and a compliance defined by a chamber into which said inertance tube opens, said compliance chamber having a volume substantially greater than that of the inertance and being disposed between said inertance tube and said binaural tubing and in direct communication with said binaural tubing.

2. A low-pass filter according to claim 1 wherein said inertance tube is cylindrical and has an internal diameter of between about 0.5 mm and 2.0 mm.

3. A low-pass filter according to claim 1 further including an exit tube communicating with said compliance chamber, said exit tube having an outer diameter sized to frictionally engage the inner diameter of said binaural tubing.

4. A low-pass filter according to claim 3 wherein said compliance chamber, said inertance tube and said exit tube are coaxial tubular cylinders.

5. A low-pass filter according to claim 4 wherein said intertance tube has an internal diameter of between about 0.5 mm and 2.0 mm.

6. A low-pass filter according to claim 5 wherein said intertance tube has an internal diameter of about 1.4 mm and a length of about 12.7 mm and wherein said compliance chamber has an internal diameter of about 19.3 mm and an internal length of about 38.6 mm.

7. A high frequency noise attenuating stethoscope comprising:
a chest piece;
a binaural tube extending from said chest piece for the transmission of sound;
two ear pieces branching from said binaural tube; and
a low-pass filter including an inertance tube in communication with said binaural tube and having an outer diameter frictionally engaging said binaural tube and an inner diameter substantially less than the inner diameter of said binaural tube; a compliance chamber in communication with said inertance tube, said compliance chamber having a volume substantially greater than that of said inertance tube and being disposed between said inertance tube and said binaural tube and in direct communication with said binaural tube, and an exit tube in communication with said compliance chamber and having an outer diameter frictionally engaging said binaural tube, said low-pass filter being located along said binaural tube closely adjacent said ear pieces and removed from said chest piece so that noise transmitted to said binaural tube from the environment in addition to sound from said chest piece must pass through said filter.

8. A stethoscope according to claim 7 wherein said inertance tube, said compliance chamber and said exit tube are coaxial tubular cylinders.

9. A stethoscope according to claim 8 wherein said inertance tube has an internal diameter of between about 0.5 mm and 2.0 mm.

10. A stethoscope according to claim 9 wherein said inertance tube has an internal diameter of about 1.4 mm and a length of about 12.7 mm and wherein said compliance chamber has an internal diameter of about 19.3 mm and an internal length of about 38.6 mm.

* * * * *